United States Patent [19]

Drent

[11] Patent Number: 4,868,328

[45] Date of Patent: Sep. 19, 1989

[54] SELECTIVE OXIDATIVE CARBONYLATION OF CONJUGATED DIENES

[75] Inventor: Eit Drent, Amsterdam, Netherlands

[73] Assignee: Shell Oil Company, Houston, Tex.

[21] Appl. No.: 123,517

[22] Filed: Nov. 20, 1987

[30] Foreign Application Priority Data

Dec. 24, 1986 [NL] Netherlands .......................... 8603301

[51] Int. Cl.$^4$ .......................... C07C 67/38; B01J 31/30; B01J 27/13
[52] U.S. Cl. .................................... 560/204; 502/169; 502/170; 502/171; 502/230; 502/324; 502/326; 560/81; 560/97; 560/193
[58] Field of Search .................... 560/81, 97, 193, 204; 502/169, 170, 171, 230, 324, 326

[56] References Cited

U.S. PATENT DOCUMENTS

| 4,189,599 | 2/1980 | Kesling, Jr. et al. | ................ 560/190 |
| 4,575,562 | 3/1986 | Hsu et al. | ............................ 560/204 |
| 4,642,371 | 2/1987 | Drent | .................................. 560/114 |

FOREIGN PATENT DOCUMENTS 2512062 9/1975 Fed. Rep. of Germany .
2064353 6/1981 United Kingdom .

*Primary Examiner*—Werren B. Lone
*Assistant Examiner*—Vera C. Clarke

[57] ABSTRACT

Process for the selective oxidative carbonylation of a conjugated diene with carbon monoxide and an alcohol in a quantity of at least 2 mol equivalents per mol diene, in the presence of a catalyst system which comprises the following components:

(a) a compound of a metal, selected from one or more platinum group metals,
(b) an oxidizing agent in the form of quinone and/or derivatives thereof, and
(c) a compound of a metal, selected from manganese or vanadium.

25 Claims, No Drawings

SELECTIVE OXIDATIVE CARBONYLATION OF CONJUGATED DIENES

FIELD OF THE INVENTION

The invention relates to a selective oxidative carbonylation of conjugated dienes and in particular to an oxidative carbonylation whereby alkene polycarboxylic esters are prepared by reaction of the diene, carbon monoxide and the compound comprising a hydroxyl group in the presence of a metal catalyst of the platinum group and a quinone derivative as oxidizing agent. The invention also relates to the catalyst systems employed therewith.

BACKGROUND OF THE INVENTION

U.S. Pat. No. 4,575,562 is directed to a process for the preparation of dimethyl adipate, which comprises reacting 1,3-butadiene with carbon monoxide under reactive temperature and pressure conditions in the presence of methanol, a catalyst which comprises a compound of the platinum metal group in a high oxidation state and an organic oxidizing agent such as a quinone, a dehydrating agent and preferably in the presence of one or more ligands, in order to form dimethyl hex-3-ene dioate inter alia, followed by hydrogenation of the dimethyl hex-3-ene dioate under the formation of dimethyl adipate. This reaction should preferably be carried out in the presence of palladium compounds. Preferred examples of ligands to be employed are: triphenyl phosphine, tri(p-methoxyphenyl) phosphine, tri(p-fluorophenyl) phosphine, tributyl phosphine, triphenyl arsine, triethyl arsine, benzonitrile, acetonitrile, propionitrile, valeronitrile, succinonitrile, glutaronitrile, triphenyl phosphite, lithium chloride, sodium bromide, lithium iodide, potassium iodide and copper chloride. Furthermore, a small quantity of an acid selected from acetic acid, trifluoroacetic acid, sulfuric acid, hydrochloric acid, hydrobromic acid or hydroiodic acid could also be employed with this process.

From the butadiene conversion and the selectivity for dimethyl hex-3-ene dioate reported in the examples of this patent, however, it will be clear to a person skilled in the art that this process cannot be considered as a particularly selective preparation with a high yield (30%, calculated on butadiene) of these desired alkene dicarboxylic acid esters, which, as starting materials for further chemical synthesis such as the preparation of adipates are becoming increasingly important. Moreover, this process is performed at relatively high pressures (34-350 atm.) and temperatures (60°-190° C.), which makes additional demands on the apparatus to be used and thus leads to higher costs.

It is known from International Patent Specification WO 80/00250 to convert conjugated diolefins (for example 1,3-butadiene) into esters to alkene polycarboxylic acids (for example dimethyl hex-3-ene dioate) by the reaction with carbon monoxide and an alcohol (for example benzyl alcohol) in the presence of a palladium catalyst, a copper(II) salt and a base, whereupon this unsaturated diester can be hydrolyzed and hydrogenated or vice versa in order to prepare a corresponding linear di-acid (for example adipic acid). The copper(II) compound should be employed in a quantity which is sufficient to oxidize the palladium(O) formed by this process back to palladium(II), and the quantity of nucleophillic base should be at least one molar equivalent of the copper(II) salt. As a copper salt, copper chloride is preferably employed. Preferred bases are alkali and alkaline earth metal salts of carboxylic acids or carbonates such as sodium acetate, potassium acetate, sodium propionate, sodium butyrate, sodium carbonate or amines such as triethylamine or lutidine.

From the examples of the process described above, it will be clear to a person skilled in the art that neither can this process be considered as a particularly selective high-yielding process for the preparation of the desired alkene dicarboxylic acid ester, such as dimethyl hex-3-ene dioate. Furthermore, the aforesaid process is characterized by relatively long reaction times (144 hours in Example I). It is therefore an object of the present invention to provide a selective conversion of butadiene of homologues thereof to the desired alkene dicarboxylic acid diester, such as diethyl or dimethyl hex-3-ene dioate and/or dimethyl hex-2-ene dioate in order to supply the ever growing need for cheaper fine chemicals as starting compounds for further chemical synthesis.

SUMMARY OF THE INVENTION

This invention relates to the selective preparation of compounds according to the formula:

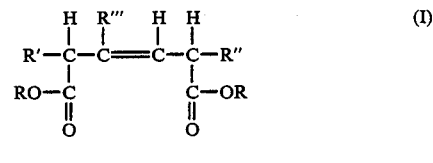

and/or

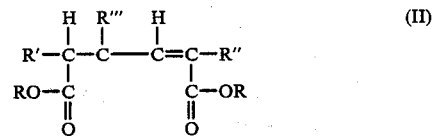

where R represents lower alkyl and preferably methyl or ethyl, or aralkyl and preferably benzyl, where R' and R" each independently represent hydrogen, lower alkyl and preferably methyl, aryl and preferably phenyl or aralkyl and preferably benzyl, and where R''' represents hydrogen or lower alkyl, which process comprises reacting a conjugated diene and in particular 1,3-butadiene, with carbon monoxide and an alcohol in a quantity of at least 2 mol equivalents per mol diene, in the presence of a catalyst system which comprises:

(a) a compound of a metal, selected from one or more platinum group metals,
(b) an oxidizing agent selected from the group consisting of quinone, derivatives of quinone, and mixtures thereof,
(c) a compound of a metal, selected from manganese or vanadium, as co-catalyst.

DESCRIPTION OF THE PREFERRED EMBODIMENTS

The expression "lower alkyl" refers to groups of 1-4 carbon atoms, the expression "aryl" to substituted or unsubstituted phenyl or naphthyl groups, and the expression "aralkyl" to phenyl or naphthyl groups, substituted with a lower alkyl group. Besides the aforesaid components of the catalyst system, small quantities of one or more dehydrating agents can, if required, also be employed and especially for the embodiments whereby the reaction is carried out in a reactor, so that in situ water is formed that adversely affects this reaction.

As used herein, the term "conjugated diene" refers to dienes having double bonds which alternate with single bonds such as, for example, 1,3-butadiene, 1,3-pentadiene, 1,3-hexadiene, 1,3-heptadiene and the like. In a preferred embodiment, the reactant in the instant invention is 1,3-butadiene.

The compound of a platinum group metal can comprise additional ligands, but it has been found that this is not necessary for optimum conversions.

Oxygen can be used to regenerate the oxidizing agent and can be added to the reactor together with the carbon monoxide or in a separate reactor. The reaction can be performed in a batchwise, continuous or semi-continuous manner. By semi-continuous is meant a reaction system in which the reactants are introduced continuously into a reactor, but no reaction products are withdrawn from the reactor until the reaction is complete. The alcohol should be employed in a quantity which is at least stoichiometric with respect to the quantity of dicarboxylic acid to be formed. Preferably, methanol or ethanol is employed as alcohol in a quantity of 2 to 10 mol per mol of diester to be formed. Small quantities of dehydrating agents can optionally be added to the reaction mixture. These serve to maintain the desired water free conditions. Examples of suitable dehydrating agents are methyl orthoformiate, metaboric acid, 2,2-dimethoxypropane, 1,4-dimethoxycyclohexane, methyl vinyl ether and 1-ethoxy-cyclohexene.

By "platinum group metal compound" is meant compounds of ruthenium, rhodium, palladium osmium, iridium, platinum and mixtures thereof. Suitable examples of platinum group metal compounds are platinum bromide, platinum chloride, palladium iodide, palladium chloride, palladium bromide and palladium acetate. Metals or metal oxides can be used directly if the reaction conditions are such that a suitable catalytic metal salt is formed during the reaction. Preferably, a palladium compound is employed as metal compound in the conversion according to the invention, and in particular palladium acetate. The platinum group metal catalyst can be homogeneous or heterogeneous. The heterogeneous form can be present as a slurry or impregnated in silicon oxide, aluminum oxide, carbon, etc. or natural or synthetic zeolites or other suitable inert materials. The metal catalyst can also be present in a polymer-bound form. The quantity of this platinum group metal catalyst component is 0.001 to 10 gram-atom per 100 mol, and preferably between 0.01 and 1.0 gram-atom per 100 mol diene.

The oxidizing agent used to keep the platinum group metal in its oxidized state can for example comprise:
1,4 benzoquinone, 2,5-dichloro-1,4-benzoquinone,
2,6-dichloro-1,4-benzoquinone, tetrachloro-1,4-benzoquinone (p-chloranil), 2,3-dicyano-1,4-benzoquinone,
2,3-dichloro-1,4-naphthoquinone, tetramethyl-1,4-benzoquinone,
2,3-dichloro-5,6-dicyano-1,4-benzoquinone,
2,5-diphenyl-1,4-benzoquinone, 4,1-naphthoquinone, 2,3-dimethyl-1,4-naphthoquinone and mixtures thereof. The aforesaid compounds can be considered as internal oxidizing agents. The preferred internal oxidizing agent is tetrachloro-p-benzoquinone (p-chloranil). Optionally, quinone/hydroquinone mixtures can also be used. The quinone, optionally mixed with hydroquinone, can be adsorbed on an inert material, such as natural or synthetic zeolites, or can be incorporated in an organic polymer. The molar ratio of the internal oxidizing agent to the platinum group metal component can vary between wide limits and generally lies in the range of 100–700 and preferably between 300 and 600. Examples of suitable manganese or vanadium compounds are manganese chloride, vanadium chloride, manganese bromide, vanadium bromide, manganese bromide, vanadium bromide, manganese acetate, vanadium acetate and mixtures thereof. Preferably, manganese chloride or vanadium chloride are employed.

The ratio of the quantities of co-catalyst to platinum group metal catalyst is not critical and can vary between wide limits. Preferably, more than 5–50 mol of the manganese or vanadium salt per gram-atom palladium is employed in order to achieve a high selectivity in combination with an attractive conversion rate. High selectivities (80%) in combination with high conversion rates are obtained if more than 10 mol and less than 45 mol of this co-catalyst per gram-atom palladium is employed.

The process according to the invention does not require the use of an additional solvent if a large excess of one of the reactants, usually the alcohol or one of the reaction products forms a suitable liquid phase. According to the preferred embodiments of the present process, however, an additional solvent is used. Any inert solvent can be used for this purpose. This can, for example, be chosen from sulfones, for example diisopropyl sulfone, tetrahydrothiophene-1,1-dioxide (sulfolane), 2-methyl-4-butyl sulfolane, 3-methyl sulfolane, 2-methyl-4-butyl solfolane; nitriles such as acetonitrile, propionitrile, benzonitrile; hydrocarbons such as benzene, toluene, xylenes, isooctane, n-hexane, cyclopentane, cyclohexane, cyclooctane; esters such as methyl acetate, ethyl acetate, methyl propionate, butyl propionate, metal benzoate, dimethyl adipate and butyrolactone; ketones such as acetone, acetophenone, 2-butanone, cyclohexanone or methyl isobutyl ketone; and ethers such as anisole, 2,5,8-trioxanone (also called diglym), diphenyl ether and diisopropyl ether. Preferably, solvents of the ether type, such as diglym, are employed.

The process according to the invention enables relatively mild reaction conditions to be employed. Temperatures in the range of 50° C. to 200° C. and in particular 50° C. to 150° C. are suitable and preferably 80° C. to 125° C. In the process according to the invention, oxygen can be used to maintain the internal oxidizing agent concentration at a high enough level to keep the platinum group metal complex in the desired higher oxidation state, i.e. in the catalytically active form for the carbonylation. The oxygen can be added with the carbon monoxide, in which case precautions to prevent the formation of explosive oxygen/carbon monoxide mixtures must be taken, or added in a separate reactor. According to another embodiment, the carbon monoxide and the oxygen can be added to the reaction in a suitable alternating manner.

It will be appreciated that no water is formed during the actual carbonylation reaction of the process, but water is formed during the oxidative regeneration of the quinone derivative from the corresponding hydroquinone derivative. If the carbonylation and the quinone regeneration take place in the same reactor, the addition of sufficient dehydrating agent is desirable in order to minimize the occurrence of side reactions, including the oxidation of butadiene or homologues or derivatives thereof. If the carbonylation and the quinone regeneration are carried out in separate reactors, the quinone-containing feedstock of the carbonylation reactor must be practically water-free. This dehydration can be carried out with the aid of the same series of aforesaid agents or by passing the quinone-containing feedstock through a suitable solid dehydrating agent or by removing the water by distillation.

The carbon monoxide can be employed in a practically pure form or mixed with oxygen and/or one or more inert gases such as nitrogen or a rare gas. The carbon monoxide pressure employed will in general be lower than that according to hitherto known processes. Pressures of 50 bar and above are preferred.

The molar ratio of the alcohol to the conjugated diene and in particular butadiene can vary between wide limits and generally lies in the range of 2:1-10:1. According to the preferred embodiments of the process, an alkanol is employed, but other alcohols can also be used successfully. The alcohol can be aliphatic, cycloaliphatic or aromatic and can optionally carry one or more inert substituents. A suitable alcohol can comprise up to 20 carbon atoms. Alkanols such as methanol, ethanol, propanol, 2,2-dihydroxymethyl-1-butanol and benzyl alcohol form suitable starting compounds. Of these, methanol and ethanol are preferred.

It will be clear from the examples given hereinafter that, with the use of manganese or vanadium compounds as co-catalyst, the average conversion rate and selectivity found for the conversion of the alkanol to the diester of hex-3-ene dicarboxylic acid and/or hex-3-ene dicarboxylic acid are surprisingly attractive relative to those obtained by the application of copper chloride, or chromium or iron compounds which an expert would consider to be similar.

It will be clear that another facet of the present invention is formed by the aforesaid specific catalyst systems as such or in the form of a solution or suspension in one of the aforesaid solvents.

The invention will now be explained with reference to the following examples, which are not to be construed as limiting the scope of the invention.

EXAMPLE 1

A 250 ml magnetically stirred Hastelloy $C^R$ autoclave was filled with 40 ml diglym, 10 ml butadiene, 15 ml ethanol, 0.1 mmol palladium acetate, 50 mmol chloranil and 4 mmol manganese chloride ($MnCl_2$). The autoclave was filled with carbon monoxide to a pressure of 60 bar, closed and heated to a temperature of 110° C. After a reaction time of 2 hours, the contents of the autoclave were analyzed by means of gas-liquid chromatography. The selectivity of the conversion of ethanol to diethyl hex-3-ene dioate and diethyl hex-2-ene dioate was 89%, while an average conversion rate of 200 mol per gram-atom Pd per hour was found.

EXAMPLE 2

In a virtually analogous manner to that described in Example 1, an experiment was performed with a catalyst system comprising 2 mmol instead of 4 mmol $MnCl_2$. The selectivity of the conversion of ethanol to diethyl hex-3-ene dioate and diethyl hex-2-ene dioate was 85%, while an average conversion rate of 155 mol per gram-atom Pd per hour was found.

EXAMPLE 3

In a virtually analogous manner to that described in Example 1, an experiment was performed in which the carbon monoxide pressure was 70 bar instead of 60 bar. The selectivity of the conversion of ethanol to diethyl hex-3-ene dioate and diethyl hex-2-ene dioate was 91%, while an average conversion rate of 170 mol per gram-atom Pd per hour was found.

EXAMPLE 4

In a virtually analogous manner to that described in Example 1, an experiment was performed with a catalyst system in which 2 mmol vanadium chloride ($VCl_3$) was included instead of 4 mmol $MnCl_2$ and the carbon monoxide pressure was 50 instead of 60 bar. The selectivity of the conversion of ethanol to diethyl hex-3-ene dioate and diethyl hex-2-ene dioate was 80%, while an average conversion rate of 130 mol per gram-atom Pd per hour was found.

By way of comparison, virtually analogous experiments were performed with 2 mmol copper chloride ($CuCl_2$), 2 mmol chromium acetoacetate ($Cr(Acac)_3$) and 2 mmol ferric chloride ($FeCl_3$) instead of 4 mmol $MnCl_2$ in the catalyst system, while the reaction time for the experiment with $CuCl_2$ was 5 hours and for the others 2 hours. The selectivity of the conversions was 72%, 90% and 30% respectively, while average conversion rates of 100, 50 and 150 mol per gram-atom Pd per hour respectively were found. Chromium acetoacetate was employed in connection with the very poor solubility of chromium chloride.

An analogous experiment without a co-catalyst gave a selectivity of 85% and an average conversion rate of 75 mol per gram-atom Pd per hour. These results demonstrate the unexpected properties of manganese and vanadium compounds as co-catalysts relative to copper, chromium, and iron compounds.

What is claimed is:

1. A process for the selective preparation of compounds according to the formula:

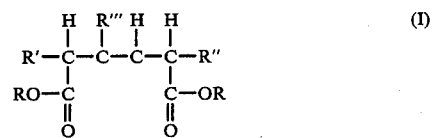

and/or

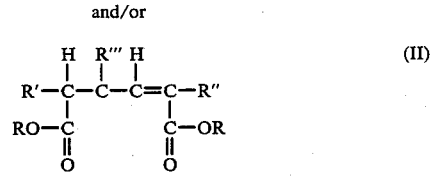

where R represents lower alkyl or aralkyl, where R' and R" each independently represent hydrogen, lower alkyl, aryl or aralkyl, and where R'" represents hydrogen or lower alkyl, which comprises reacting at a temperature in the range of from about 80° C. to about 125° C. and a pressure of at least about 50 bar a conjugated diene with carbon monoxide and an alcohol in a quantity of at least 2 mol equivalents per mol diene, in the presence of a catalyst system which comprises:

(a) at least one platinum group metal compound in an amount of from about 0.001 to about 10 gram-atom platinum group metal compound per 100 mol of diene,
(b) an oxidizing agent selected from the group consisting of quinone, derivatives of quinone and mixtures thereof, wherein said oxidizing agent is present in a molar ratio to platinum group metal compound between about 100 and about 700, and
(c) a co-catalyst selected from the group consisting of a manganese metal compound, a vanadium metal compound and mixtures thereof, in an amount of from about 5 to about 50 mol of co-catalyst per gram-atom of platinum group metal compound.

2. The process of claim 1, wherein R is selected from the group consisting of methyl and ethyl, R' and R" are selected from the group consisting of hydrogen and methyl, and R''' is selected from the group consisting of hydrogen and methyl.

3. The process of claim 1 wherein said conjugated diene is 1,3-butadiene.

4. The process of claim 1 wherein said catalyst system additionally contains small quantities of at least one dehydrating agent.

5. The process of claim 4 wherein said dehydrating agent is selected from the group consisting of methyl orthoformiate, metaboric acid, 2,2-dimethoxypropane, 1,4-dimethoxycyclohexene, methyl vinyl ether and 1-ethoxy-cyclohexene.

6. The process of claim 1 wherein said platinum group metal compound is selected from the group consisting of palladium iodide, palladium chloride, palladium bromide, palladium acetate, platinum bromide, platinum chloride and mixture thereof.

7. The process of claim 6 wherein said platinum group metal compound is palladium acetate.

8. The process of claim 1 wherein said oxidizing agent is selected from the group consisting of
1,4 benzoquinone, 2,5-dichloro-1,4-benzoquinone,
2,6-dichloro-1,4-benzoquinone, tetrachloro-1,4-benzoquinone (p-chloranil), 2,3-dicyano-1,4-benzoquinone,
2,3-dichloro-1,4-naphthoquinone, tetramethyl-1,4-benzoquinone,
2,3-dichloro-5,6-dicyano-1,4-benzoquinone,
2,5-diphenyl-1,4-benzoquinone, 1,4-naphthoquinone,
2,3-dimethyl-1,4-naphthoquinone and mixtures thereof.

9. The process of claim 8 wherein said oxidizing agent is p-chloranil.

10. The process of claim 1 wherein a quantity of said platinum group metal compound of about 0.01 to about 1.0 gram-atom per 100 mol diene is used.

11. The process of claim 1 wherein said co-catalyst is selected from the group consisting of manganese chloride, vanadium chloride, manganese bromide, vanadium bromide, manganese acetate, vanadium acetate and mixtures thereof.

12. The process of claim 11 wherein said co-catalyst is selected from the group consisting of manganese chloride and vanadium chloride.

13. The process of claim 1 wherein a molar ratio of alcohol to conjugated diene in the range of from about 2:1 to about 10:1 is used.

14. The process of claim 1 wherein said alcohol is selected from the group consisting of methanol and ethanol.

15. A catalyst system for the oxidative carbonylation of a conjugated diene with carbon monoxide and an alcohol, said catalyst system comprising:
(a) at least one platinum group metal compound in an amount of from about 0.001 to about 10 gram-atom platinum group metal compound per 100 mol of diene,
(b) an oxidizing agent in the form of quinone and/or derivatives thereof, wherein said oxidizing agent is present in a molar ratio to said platinum group metal compound between about 100 and about 700, and
(c) a co-catalyst selected from the group consisting of a manganese metal compound and a vanadium metal compound, in an amount of from about 5 to about 50 mol of co-catalyst per gram-atom of platinum group metal compound.

16. The catalyst system of claim 15 wherein said catalyst system additionally contains small quantities of at least one or more dehydrating agents.

17. The catalyst system of claim 16 wherein said dehydrating agent is selected from the group consisting of methyl orthoformiate, metaboric acid, 2,2-dimethoxypropane, 1,4-dimethoxycyclohexane, methyl vinyl ether and 1-ethoxy-cyclohexene.

18. The catalyst system of claim 15 wherein said platinum group metal compound is selected from the group consisting of palladium iodide, palladium chloride, palladium bromide, palladium acetate, platinum bromide and platinum chloride.

19. The catalyst system of claim 18 wherein said platinum group metal compound is palladium acetate.

20. The catalyst system of claim 15 wherein said oxidizing agent is selected from the group consisting of
1,4 benzoquinone, 2,5-dichloro-1,4-benzoquinone,
2,6-dichloro-1,1,4-benzoquinone, tetrachloro-1,4-benzoquinone (p-chloranil), 2,3-dicyano-1,4-benzoquinone,
2,3-dichloro-1,4-naphthoquinone, tetramethyl-1,4-benzoquinone,
2,3-dichloro-5,6-dicyano-1,4-benzoquinone,
2,5-diphenyl-1,4-benzoquinone, 1,4-naphthoquinone,
2,3-dimethyl-1,4-naphthoquinone and mixtures thereof.

21. The catalyst system of claim 20 wherein said oxidizing agent is p-chloranil.

22. The catalyst systems of claim 15 wherein said co-catalyst is selected from the group consisting of manganese chloride, vanadium chloride, manganese bromide, vanadium bromide, manganese acetate, vanadium acetate and mixtures thereof.

23. The catalyst system of claim 22 wherein said co-catalyst is selected from the group consisting of manganese chloride and vanadium chloride.

24. The catalyst system of claim 15 wherein a molar ratio of oxidizing agent to platinum group metal compound between about 300 and about 600 is used.

25. The catalyst system of claim 15 wherein said catalyst system additionally contains diglym as solvent.

* * * * *